United States Patent [19]

Sluijter et al.

[11] Patent Number: 5,571,147
[45] Date of Patent: *Nov. 5, 1996

[54] THERMAL DENERVATION OF AN INTERVERTEBRAL DISC FOR RELIEF OF BACK PAIN

[76] Inventors: Menno E. Sluijter, Stadionkade 6, 1077, VG Amsterdam, Netherlands; Eric R. Cosman, 872 Concord Ave., Belmont, Mass. 02178

[ * ] Notice: The term of this patent shall not extend beyond the expiration date of Pat. No. 5,433,739.

[21] Appl. No.: 303,956

[22] Filed: Sep. 9, 1994

Related U.S. Application Data

[63] Continuation-in-part of Ser. No. 146,875, Nov. 2, 1993, Pat. No. 5,433,739.

[51] Int. Cl.[6] .................................................. A61F 7/00
[52] U.S. Cl. .......................... 607/99; 607/96; 607/113; 604/21
[58] Field of Search .................... 128/DIG. 27; 607/89, 607/99; 604/20

[56] References Cited

U.S. PATENT DOCUMENTS

| | | | |
|---|---|---|---|
| 4,802,475 | 2/1989 | Weshahy | 128/DIG. 27 X |
| 5,327,884 | 7/1994 | Hardy et al. | 607/89 X |
| 5,330,517 | 7/1994 | Mordon et al. | 607/89 |
| 5,395,362 | 3/1995 | Sacharoff et al. | 604/20 X |
| 5,433,739 | 7/1995 | Sluijter et al. | 607/99 |

*Primary Examiner*—Angela D. Sykes
*Assistant Examiner*—Ryan Carter
*Attorney, Agent, or Firm*—Richard J. Birch

[57] ABSTRACT

This continuation-in-part patent application follows the original parent patent application which described a general method of denervation of the nerves in and around the intervertebral disc to relieve back pain using heating from a probe which is inserted within the intervertebral disc. The probe in the original application can be connected to a power source to deliver energy to the disc, thereby heating the disc and denervating the nerves associated with the disc, with consequent relief of various kinds of discogenic pain. This continuation-in-part illustrates other embodiments of the invention described in the parent patent application. In particular, it describes other embodiments of heating methods to denervate the disc, as well as thermal cooling or cryogenic methods to denervate the disc. These methods can be either percutaneous or carried out during open interoperative intervention of the disc. Furthermore, we describe in this continuation-in-part an embodiment of the impedance-detecting probes and shafts which were generically described in the parent patent application. The impedance measuring method and devices can help in ascertaining when the thermal probe is in the proper position within the intervertebral disc to make the thermal lesion.

7 Claims, 1 Drawing Sheet

THERMAL DENERVATION OF AN INTERVERTEBRAL DISC FOR RELIEF OF BACK PAIN

This is a continuation-in-part of application Ser. No. 08/146,875 filed on Nov. 2, 1993, now U.S. Pat. No. 5,433,739.

BACKGROUND TO THE INVENTION

In the parent patent application to this continuation-in-part, a method and apparatus were described in general terms which involves placing a probe in proximity to or within the intervertebral disc to thermally denervate the nerves that enervate the disc, such nerves being inside the disc and/or on the approximate surface of the disc. In the embodiments shown in the parent patent application, various types of thermal probes or heating probes were introduced into the disc, and the temperature of the disc or a portion of the disc was elevated so as to destroy the nerves in and/or on the disc which are giving rise to the discogenic pain. In one specific embodiment, a radiofrequency probe was shown to be inserted into the disc, and the probe, upon proper target location inside the disc, was connected to an external radiofrequency power source, thus producing controlled heating within the disc. This has been shown clinically by the present authors to be an effective and safe method for relieving various kinds of discogenic pain in the lower back, thoracic, and cervical regions of the spine.

The parent patent application describes several specific embodiments of disc heating devices and states that further embodiments may be devised by those skilled in the art which also fall within the scope of that parent application that have the objective of heating the disc until it is denervated. In this continuation-in-part, we wish to extend the concepts of thermal denervation of the disc to that of lowering the temperature or, in essence, freezing the disc cryogenically for the same pain relief objective. Furthermore, we wish to elaborate on the use of other power sources that can be used to cause heating of the disc which were generally stated and observed in the parent patent application. In that parent patent application, reference was made to use of penetrating radiation to heat the disc. We would like to describe a specific embodiment of this involving electromagnetic radiation and particularly the use of optical, or near optical, radiation such as applicable with lasers.

DESCRIPTION OF THE INVENTION

The following illustrations are merely examples of extensions of the parent patent application and can be further extended by those skilled in the art, but still remain within the scope of the present claims and claims of the parent patent application.

Figure 1:
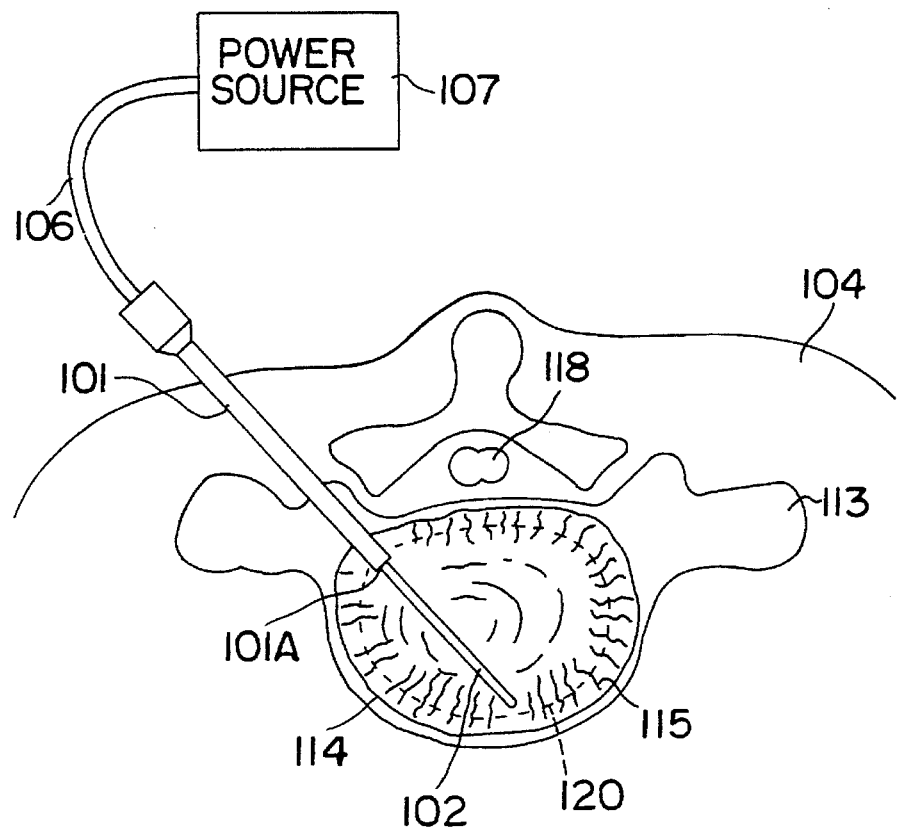
FIG. 1 shows a thermal probe, cryogenic or heating, inside the disc for the purpose of denervation in and around the disc. The probe could be cryogenic, laser, rf, or any other thermal system.

Referring to FIG. 1, a probe 101 is inserted through the tissue 104 of the body, and its tip 101A either approximates the external portion of the disc 114 or enters the interior region of the disc itself. This probe or cannula may have been introduced with an obdurating stylet. Once the stylet is removed, another probe 102 may be inserted through the cannula 101, and this probe may further extend within the disc 114, as shown in FIG. 1. This was a physical embodiment described and used as an illustration of the invention of the parent patent application. As described previously, this probe 102 can be connected via a connection means 106 to a power source 107, which may be external to the body so as to deliver heat to the intervertebral disc, giving rise to a heat zone indicated by the dashed perimeter 120, and thereby making possible the denervation or destruction of the nerves 115 which are around the external surface of the disc 114 and may actually penetrate into the disc a distance. In this continuation-in-part, the example we would like to cite is that probe 102 is a fiber which can carry and transmit energy in the laser range to the disc; that is to say, the energy delivered to the probe in the form of optical or near-optical electromagnetic energy. The energy may be of other electromagnetic sources such as microwave, far-infrared, ultraviolet, etc. The connection means 106 in the case of the laser might be a light-carrying fiber optic tube. The tip end 102 may be a fiber optic tube or fiber which enables scattering of the laser light into the disc. The disc absorbing this laser energy will heat up, therefore causing a zone of heating indicated generically by the dashed surface 120, thereby heating and killing or denervating the pain-carrying fibers 115. Apparatus 107 would therefore be the power source for the laser light or other electromagnetic energy.

Also referring to FIG. 1, the same configuration generically could apply to the application of cryogenic cooling to the disc. Cannula 101 might be the introducing cannula in that case. Cannula or tube 102 could be a cryogenic tube, inside of which is circulated cryogenic fluid or other cryogenic agents which are carried by the tube means or channel means 106 from cryogenic source 107. When the tip of probe 102 becomes very cold, it will begin to freeze a region of the disc around the tip. That might be indicated by the dashed contour 120. When this contour extends into the enervated region of the disc, including the nerves 115, the nerves will be destroyed by the freezing. Freezing has the advantage that it can be visualized easily by ultrasound scanning, and thus one of the aspects of the present invention would be to insert a cryogenic probe into the disc for the purpose of cryogenic denervation of the disc and simultaneously watch the ice ball or the freezing zone expand within the disc using ultrasound, MRI, or other imaging means in a real-time mode. Thereby, the extent of the freezing zone can be determined as the procedure goes on, and the freezing can be stopped when the appropriate zone of extension has been achieved. It is known that in the case of cryogenics, the cryogenic probe may have hollow inner tubes which can carry cryogenic gas or fluids such as liquid nitrogen, which is supplied by a cryogenic apparatus outside of the body. The circulation of this cooling agent into the probe can, for example, cool the tip of the probe which is included within the disc. This causes very significant cooling of the tissue surrounding the tip of the probe and, indeed, can freeze that portion of the tissue that is in proximity to the tip, thus killing neural structures within the freezing zone or within the substantially cooled zone which is close to the totally frozen zone. This is a well known method for ablating tumors and other structures within the body, but has never been used within the disc for the purpose of denervating the disc by insertion of a cryogenic probe within the disc itself. Interventive MRI scanning can also be used to monitor virtually real-time the process of the radiofrequency technique, since the heating zone can, in some cases, be visualized directly in real-time on the MRI image by use of "turboflash" imaging and other imaging sequences. Thus, it is the intention that the scope of this continuation-in-part patent to include the situation of a probe inserted into the disc for the purpose of any type of thermal denervation, whether that denervation be accomplished by heating or by cooling. All the geometric factors which are described in the parent patent application, including adjunct stimulation and impedance probes, thermal monitoring probes placed in the main cannulas or on secondary cannulas, the use of curved probes, or probes which arc around within the disc so as to maximally ablate the neural structures are included within the scope of this patent application. The same comments and adjuncts which apply to cryogenics and heating can apply to the heating probe associated with a laser or other antenna means for microwave or other electromagnetic sources or ultrasonic probes placed into the disc for the purpose of ablating the neural structures within the disc.

It is also within the scope of this and the parent patent application that multiple probes could be placed in the disc, for example, probes placed bilaterally for better heating or cooling coverage, or multiple parallel probe or probes placed stereotactically when preplanning or real-time imaging with X-rays or ultrasound or other imaging techniques are used; all such embodiments and methods are included within the scope of this patent. MRI compatible probes or probes which are ecogenic and thus which can be favorably seen under ultrasonic or other imaging techniques are obviously included within the scope of this and the parent application. As pointed out above, in the case of interventive MRI imaging, real-time monitoring of the heat process can be done. This can apply to radiofrequency heating or other heating or cooling techniques and are obviously included within the scope of this and the parent patent application. Included here are the processes and apparatus associated with radiofrequency, microwave, ultrasonic, or laser probes for the purpose of heating the disc, and the extensive heat zone could be monitored real time during the process of the procedure, and therefore stopped or monitored when the proper extent of heating has been achieved.

Figure 2A:
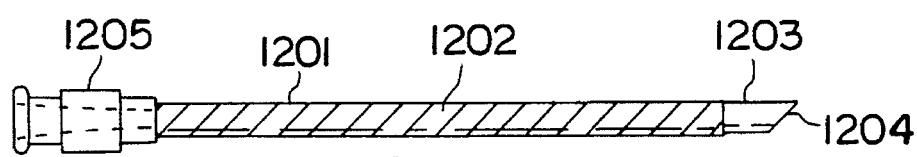
FIGS. 2a, 2b, and 2c show a system of components for rf disc heating or any other rf heating, thermal ablation, or cryogenic denervation including a cannula, impedance stylet, and thermal probe.
Figure 2B:
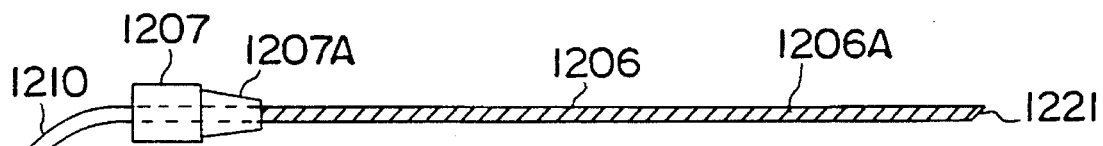
Figure 2C:
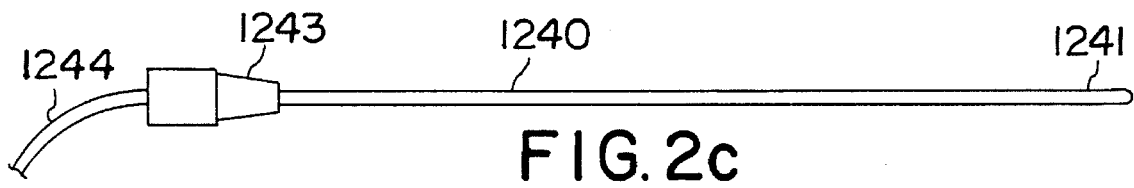

Referring to FIGS. 2a, 2b and 2c, a set of instruments is shown which fall under the general scope of the claims of the parent patent application and, in this specific embodiment, some notable points can be made here. The cannula 1201 may be circular and of a metal tubular shape, and it may be insulated, as shown by insulation 1202, over most of its shaft with an exposed end tip portion 1203, which could be used to deliver radiofrequency or other power source means so as to heat the disc. There is a beveled point 1204 at the end of the cannula, and the hub 1205 may be of a radiolucent material, although this is not a requirement of the probe for the purpose of heating the disc. Shown also is a special stylet 1206 which fits into the cannula 1201 and may be used during the insertion process into the disc. The cannula 1206 has an insulation over most of its surface indicated by the hatched lines 1206A, and the beveled tip 1221 may have an exposed metal surface which is front-facing. The hub 1207 has a luer portion, as in illustration 1207A, which fits into the female portion of the hub 1205, and there is a connection wire 1210 which connects to the metal inner shaft of the insulated stylet 1206. When such an insulated stylet is inserted into cannula 1201 and the assembly is inserted into the disc, then the impedance from the small, front-facing, uninsulated portion 1221 of the stylet can be used to very carefully monitor the change in impedance when passing from tissue outside of the disc into the interior of the disc. The impedance change is very significant, and because the area 1221 is very small, it would enable this interface to be detected very exactly. As the probe and stylet are advanced further into the disc, it would reach the far side of the disc wall and, again, as the needle approaches that point, a change in impedance would be noted. Thus, the approach to both the entry point and the exit point of the disc can be detected by this insulated, impedance-monitoring stylet with its small, front-facing, impedance-sensitive, exposed surface. This procedure of tracking the impedance across the depth span of the disc would enable proper placement of the disc, and possibly even determination of the proper tip exposure that one would wish on a lesion electrode within the disc. Indeed, the length of the tip portion 1203 on the main cannula could be made variable by having a sliding insulative sleeve or a cannula within a cannula to vary the tip exposure for radiofrequency heating. A similar embodiment could be made in the case of laser heating, cryogenics, or any other methodology. In FIG. 2c is shown another probe which can be inserted into the cannula 1201 once that cannula is properly placed within the disc. This probe 1240 could be radiofrequency, cryogenic, ultrasonic, laser delivery, or any other modality which is generally described for heating or cooling of the disc or other physical modalities that may be thought of by those skilled in the art. Its tip end 1241 can be extended out beyond the tip end 1204 of the cannula, thus giving varying depth penetration within the disc and also varying heating capacity or capabilities within the disc, depending on the disc dimension and the extent that the lesion should be made. The embodiments of FIGS. 2a, 2b, and 2c show a set of instruments which can be used for basic introduction, impedance monitoring, stimulation on the way in, and, ultimately, a tool for doing the heating or cooling. All of these elements could be incorporated in one unitized assembly where all these functions, rather than being separated by one element to another, could be incorporated in one unitized assembly. All of the ancillary technology and methodology described in the parent application can be applied and mapped over into the case of laser or cryogenic heating or any other methodology that one skilled in the art could consider or implement, which is generally included under the teachings and claims of this continuation-in-part and parent application.

It should be pointed out that all of these tools and methodology can be used both percutaneously and in open surgery. For example, if one performs a percutaneous discectomy using an instrument such as the Nucleotome, which removes disc material, these tools could be used in conjugation with such a device for denervating the disc after tissue removal. Alternatively it is intended that this invention include apparatus, methods, and situations including a percutaneous or interoperative disc removal device in conjugation with or integrated with a heating or cooling device such that before, during, or after disc material is removed by the former device, thermal denervation of the disc may be performed by the latter device. Furthermore, if an open laminectomy is performed wherein the disc is exposed and tissue is removed surgically, as is commonly done, such thermal probes or instruments for thermal delivery could be inserted within the open disc and in the region of the disc that has not been resected for the purpose of denervating those remnant disc portions. This could alleviate the syndrome of post-surgical disc pain. Thus, the method of denervating the disc by heating or cooling by means of a probe or probes or other instruments that can be inserted into the disc which may not be shaft-like or probe-like, but rather like scoops, scalpels, forceps, etc., is also included within the scope of this patent; this applying in conjugation with either open surgery or percutaneous surgery of the disc.

Therefore, having described the various embodiments in this continuation-in-part, we state that those skilled in the art can make variations thereof which still fall within the scope and claims of this and the parent patent application. Therefore,

What we claim by U.S. Letters Patent are the following claims:

1. A method of treating back or neck pain by cooling an intervertebral disc, including:
   (a) inserting a probe into said intervertebral disc, said probe being adapted to be connected to an external apparatus which can enable cooling of said probe so as to cool said intervertebral disc;
   (b) connecting said external apparatus to said probe, causing cooling of said intervertebral disc, which thereby causes relief of said back or neck pain.

2. The method of claim 1 in which said probe is a cryogenic probe, and said external apparatus is a source of cryogenic fluid or gas, and further including the step of allowing said cryogenic fluid or gas to flow into said cryogenic probe so as to cool a portion of said cryogenic probe that is within said intervertebral disc, and thus freezing and cooling said intervertebral disc so as to denervate a portion of said intervertebral disc and thus relieve said neck or back pain.

3. A method of treating back or neck pain of the patient by heating an intervertebral disc including:
   (a) inserting a probe into said disc, said probe being adapted to be connected to an external laser source which can deliver laser power through said probe to said disc so as to heat said disc;
   (b) applying said laser power from said external laser source to said disc via said probe, causing heating of said disc which thereby causes relief of said back or neck pain.

4. The method of claim 3 wherein said probe includes a laser-carrying fiber or channel, and further including the step of connecting said external laser source to said probe so as to cause laser light from said external laser source to pass through said laser-carrying fiber or channel, said laser light being deposited into said disc and thereby causing heating of said disc.

5. A probe system adapted for heating the intervertebral disc of a patient, including:

(a) a cannula having a near end and a far end, and having an open end at the cannula's far end and having a substantially radiolucent cannula hub at the near end of said cannula;
   (b) a stylet having a near end and a far end, said stylet fitting into said cannula so that the stylet's far end occludes said open end at said cannula's far end, said stylet having a substantially radiolucent stylet hub, and said stylet having an electrically uninsulated impedance-monitoring tip at said stylet's far end which will contact tissue of the patient in the region of said cannula's far end when said cannula is inserted into said patient, said stylet having a stylet connection means at said stylet's near end which is adapted to be connected to said impedance-monitoring tip and to be connected to external impedance-monitoring apparatus; whereby, when said stylet is inserted into said cannula, and said cannula is inserted into said disc, said radiolucent hubs enable substantially unobstructed guidance of said cannula and said stylet by X-ray images of said cannula's far end within said disc, and whereby the electrical impedance of said tissue near said cannula's far end can be monitored so as to determine when said cannula's far end is properly within said disc;
   (c) a power delivery means adapted to be connected to said cannula and to an external power apparatus which enables power to be transferred from said external power apparatus to said cannula's far end, and which thereby causes heating of said disc when said cannula's far end is within said disc, thereby to relieve the pain of said patient related to said disc.

6. The apparatus of claim 5 wherein said cannula is substantially insulated on its surface and has an uninsulated electrically conductive tip at said cannula's far end, said power delivery means being an electrical connection means adapted to connect said uninsulated electrically conductive tip to said external power apparatus, said external power apparatus being a source of electrical current, such that when said cannula's far end is within said disc, said electrical current can be transmitted to said disc through said electrical connection means and said uninsulated electrically conductive tip so as to heat said disc.

7. The apparatus of claim 5 wherein said power delivery means is a conduit of laser light and said external power apparatus is a laser light source, such that when said cannula's far end is within said disc, said laser light can be transmitted to said disc by said conduit, and the power from said laser light source will heat said disc.

* * * * *